(12) United States Patent
Rapp

(10) Patent No.: US 9,863,921 B2
(45) Date of Patent: Jan. 9, 2018

(54) FLUID INTERFACE BETWEEN FLUID LINES OF DIFFERING CROSS-SECTIONAL AREA

(71) Applicant: AGILENT TECHNOLOGIES, INC., Loveland, CO (US)

(72) Inventor: Holger Rapp, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 640 days.

(21) Appl. No.: 13/974,549

(22) Filed: Aug. 23, 2013

(65) Prior Publication Data

US 2014/0083173 A1 Mar. 27, 2014

(30) Foreign Application Priority Data

Sep. 26, 2012 (DE) .................. 10 2012 217 487

(51) Int. Cl.
*G01N 30/38* (2006.01)
*G01N 30/62* (2006.01)
(Continued)

(52) U.S. Cl.
CPC ........ *G01N 30/38* (2013.01); *B01L 3/502715* (2013.01); *B01L 3/502746* (2013.01);
(Continued)

(58) Field of Classification Search
CPC ..... B01L 2300/0864; B01L 2400/0487; B01L 3/502715; B01L 3/502746; G01N 2030/6013; G01N 30/38; G01N 30/6017; G01N 30/62; Y10T 137/0318; Y10T 137/85938; G01L 1/125; G01L 9/0041; G01L 9/16; A61B 2562/0247; A61B 5/02141; A61B 5/6824
See application file for complete search history.

(56) References Cited

U.S. PATENT DOCUMENTS 4,883,409 A 11/1989 Strohmeier et al.
6,221,654 B1 * 4/2001 Quake ............. G01N 27/44791
366/DIG. 3

(Continued)

FOREIGN PATENT DOCUMENTS

EP 0309596 A1 3/1993

*Primary Examiner* — Randy Gibson
*Assistant Examiner* — Gedeon M Kidanu

(57) ABSTRACT

A fluid transfer device transfers a fluid from a first fluid channel with a first cross-sectional area into a second fluid channel with a second cross-sectional area, larger than the first cross-sectional area. The fluid transfer device includes a fluid inlet interface at which the fluid is transferable from the first fluid channel into the fluid transfer device; an inlet branch configured to split the fluid from the first fluid channel into multiple inlet branch channels; multiple outlet branches, each of which is configured to split the fluid from the inlet branch channels into respective outlet branch channels; and a fluid outlet interface configured to transfer the fluid in the outlet branch channels into the second fluid channel. The inlet and output branches and branch channels are disposed such that the fluid exits from the fluid outlet interface, distributed in a two-dimensional manner across the second cross-sectional area.

19 Claims, 2 Drawing Sheets

(51) Int. Cl.
  *G01L 1/12* (2006.01)
  *B01L 3/00* (2006.01)
  *G01N 30/60* (2006.01)

(52) U.S. Cl.
  CPC .............. *G01L 1/125* (2013.01); *G01N 30/62* (2013.01); *B01L 2300/0864* (2013.01); *B01L 2400/0487* (2013.01); *G01N 30/6017* (2013.01); *G01N 2030/6013* (2013.01); *Y10T 137/0318* (2015.04); *Y10T 137/85938* (2015.04)

(56) References Cited

U.S. PATENT DOCUMENTS

| | | | | |
|---|---|---|---|---|
| 6,923,907 | B2* | 8/2005 | Hobbs | B01F 13/0059 210/198.2 |
| 7,968,287 | B2* | 6/2011 | Griffiths | B01F 3/0807 435/180 |
| 8,784,012 | B2* | 7/2014 | Toner | B01D 21/0087 356/246 |
| 2002/0034748 | A1* | 3/2002 | Quake | B01L 3/502707 435/6.12 |
| 2002/0037499 | A1* | 3/2002 | Quake | B01F 5/0646 435/6.13 |
| 2002/0058332 | A1* | 5/2002 | Quake | B01L 3/502784 435/288.5 |
| 2003/0118486 | A1* | 6/2003 | Zhou | B01J 19/0046 422/400 |
| 2003/0133358 | A1* | 7/2003 | Karp | B01F 5/0471 366/341 |
| 2003/0138359 | A1* | 7/2003 | Chow | B01L 3/502784 422/400 |
| 2005/0032238 | A1* | 2/2005 | Karp | B01L 3/5025 436/177 |
| 2005/0048669 | A1* | 3/2005 | Hobbs | G01N 30/6026 436/180 |
| 2006/0171654 | A1* | 8/2006 | Hawkins | G01N 21/05 385/147 |
| 2008/0108122 | A1* | 5/2008 | Paul | B01F 5/0475 435/183 |
| 2009/0014360 | A1* | 1/2009 | Toner | B01D 21/0087 209/208 |
| 2009/0281250 | A1* | 11/2009 | DeSimone | C08G 59/30 525/418 |
| 2010/0277722 | A1* | 11/2010 | Kraiczek | B81C 1/00071 356/244 |
| 2011/0023970 | A1* | 2/2011 | Rapp | B01L 3/502738 137/13 |
| 2011/0039303 | A1* | 2/2011 | Jovanovich | B82Y 30/00 435/91.2 |
| 2012/0149021 | A1* | 6/2012 | Yung | B03C 1/01 435/6.12 |
| 2014/0026968 | A1* | 1/2014 | Abate | B01L 3/502784 137/1 |

* cited by examiner

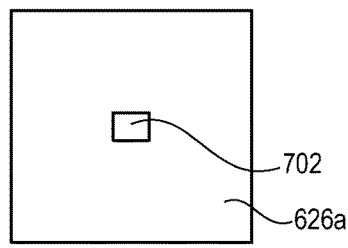
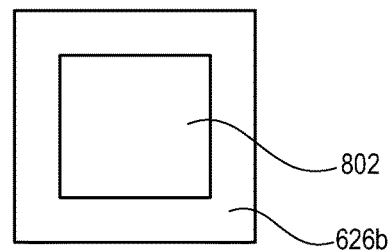
Fig. 7   Fig. 8
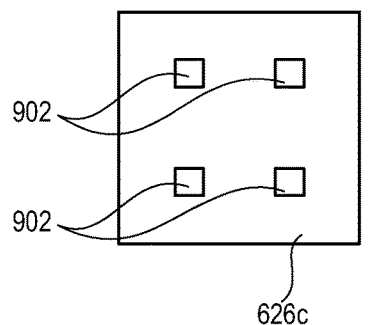
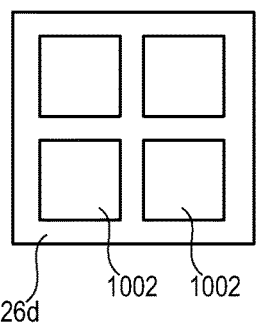
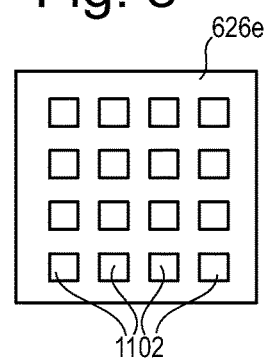
Fig. 9   Fig. 10   Fig. 11
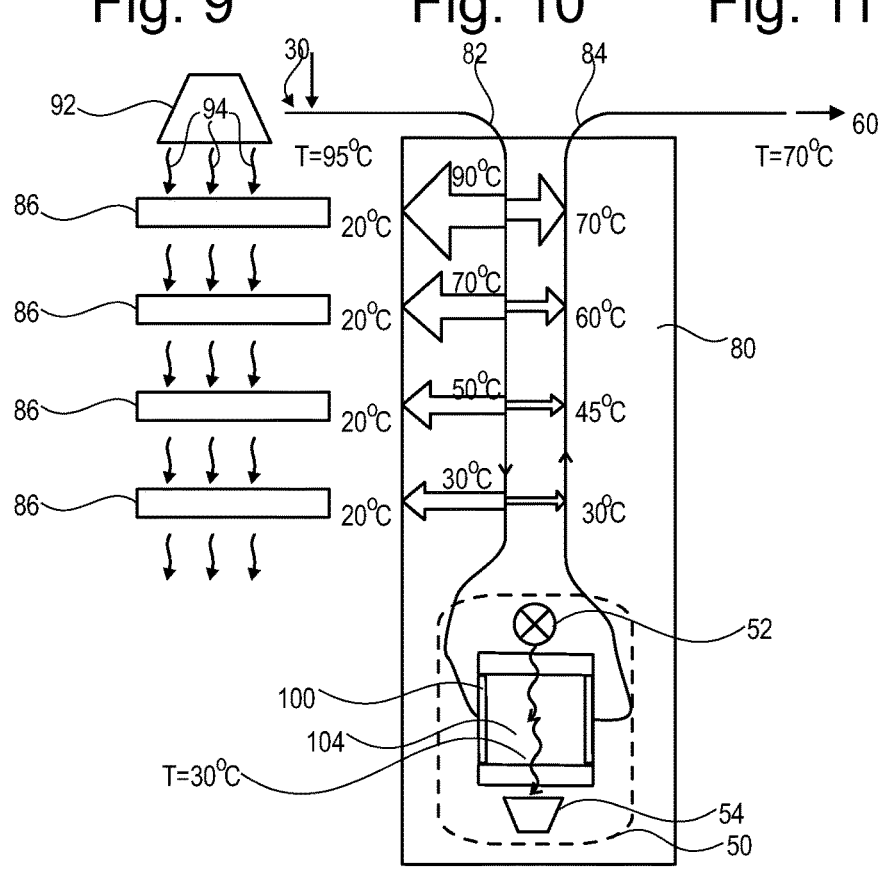
Fig. 12

FLUID INTERFACE BETWEEN FLUID LINES OF DIFFERING CROSS-SECTIONAL AREA

CROSS-REFERENCE TO RELATED APPLICATIONS

A claim for priority under 35 U.S.C. §119 is made to German Patent Application DE 102012217487.7, filed Sep. 26, 2012, in the German Patent and Trademark Office, the entire contents of which are hereby incorporated by reference.

BACKGROUND

Various embodiments relate to a fluid transfer device, a flow cell, a sample separation device and a method of operating the same.

In high-performance liquid chromatography (HPLC), a fluid (mobile phase) is typically moved through a stationary phase (for example, a chromatographic separation column) at a precisely controlled flow rate (for example, in the region of microliters or milliliters per minute) and at a high pressure (for example, 20 bar to 1000 bar and beyond, currently up to 2000 bar), at which the compressibility of the fluid is perceptible, in order to separate from one another individual components of a sample liquid introduced into the mobile phase. Detection of the separated fractions of the sample then takes place in a flow cell of a liquid chromatography device. For this purpose, the fluid sample is conveyed from a capillary downstream of the chromatographic separation column into a container of the flow cell. While the fluid sample is passing through the flow cell, a fluorescence measurement of the fluid sample can be performed, with which the individual fractions of the fluid sample can be identified or quantified.

An example of such an HPLC system is described by EP 0,309,596 B1 of the same applicant, Agilent Technologies, Inc., the entire contents of which are hereby incorporated by reference.

During the transfer from the capillary downstream of the chromatographic separation column to the flow cell, the fluid is transferred from the capillary, which has a small cross-sectional area, into the flow cell container, which has a much larger cross-sectional area. Due to the sudden widening of the diameter of the fluid line, undesired effects often occur at this fluid interface, such as turbulence of the fluid sample, the occurrence of a turbulent flow or the formation of a dead volume through which the fluid sample does not flow. Both may cause artifacts, and thus reduce detection accuracy of the liquid chromatography device. Similar and other problems may also arise with other applications, where a fluid is transferred from a fluid line having a smaller diameter into a fluid line having a larger diameter.

In fluid handling devices, an artifact-free and dead-volume-free transfer of a fluid between fluid lines of differing cross-sectional areas is thus still difficult.

SUMMARY

Illustrative embodiments of the invention enable the transfer of a fluid between fluid channels of differing diameter with a small dead volume and without undesired effects on a detection of the fluid.

According to a representative embodiment, a fluid transfer device transfers a fluid (i.e. a liquid and/or a gas, optionally comprising solid particles, for example a fluid sample) from a first fluid channel with a first cross-sectional area (i.e., an area, normal to a flow direction of the fluid, of the first fluid channel through which the fluid flows) at the outlet side (in the flow direction of the fluid) into a second fluid channel with a second cross-sectional area (i.e., an area, normal to a flow direction of the fluid, of the second fluid channel through which the fluid flows) at the inlet side (in the flow direction of the fluid), the second cross-sectional area being larger than the first cross sectional area. For example, the ratio between the second cross-sectional area and the first cross-sectional area can be at least two, in particular, or at least five). The fluid transfer device comprises a fluid inlet interface (i.e., an inlet at which flowing fluid can flow into the fluid transfer device), at which the fluid can be transferred out of the first fluid channel into the fluid transfer device, an inlet branch (in particular a fluid splitter, for example, with a characteristic of a T-piece or a Y-piece) fluidically coupled with the fluid inlet interface, which inlet branch splits fluid from the first fluid channel into a plurality of inlet branch channels, a plurality of outlet branches (in particular fluid splitters, for example, each with a characteristic of a T-piece or a Y-piece) fluidically coupled with the inlet branch channels (in particular indirectly by at least one further branch and/or by at least one further branch channel, or directly), where each of the outlet branches splits fluid from a particular one of the inlet branch channels in each case into a plurality of outlet branch channels, and a fluid outlet interface (i.e., an outlet at which flowing fluid can flow out of the fluid transfer device) fluidically coupled with the outlet branch channels, at which fluid outlet interface the fluid can be transferred out of the fluid transfer device into the second fluid channel. The branches (i.e., the inlet branch, outlet branches, optionally one or more planes with intermediate branches) and the branch channels (i.e., the inlet branch channels, outlet branch channels, optionally one or more planes with intermediate branch channels) are disposed in such a way that the fluid exits, distributed in a two-dimensional manner over the second cross-sectional area (in particular, distributed essentially uniformly over a two-dimensional area), out of the fluid outlet interface.

According to another representative embodiment, a flow cell is provided for detecting a fluid which can be fed from a first fluid channel with a first cross-sectional area at the outlet side. The flow cell comprises a second fluid channel with a second cross-sectional area at the inlet side, which is larger than the first cross-sectional area, a fluid transfer device with the features described above for transferring the fluid from the first fluid channel into the second fluid channel, and a detection device which is adapted for detecting information indicative of a property of the fluid (in particular, for the qualitative or quantitative detection of fractions of the fluid) by interaction with the fluid flowing along the second fluid channel.

According to a further exemplary embodiment, a sample separation device is provided for separating fractions of a fluid. The sample separation device comprises a separation device for separating different fractions of the fluid, where the separated fluid is feedable to a first fluid channel with a first cross-sectional area at the outlet side, and a flow cell with the features described above for detecting the fluid feedable from the first fluid channel.

According to a further representative embodiment, a method is provided for transferring a fluid from a first fluid channel with a first cross-sectional area at the outlet side into a second fluid channel with a second cross-sectional area at the inlet side, the second cross-sectional area being larger than the first cross-sectional area. According to the method, the fluid is transferred out of the first fluid channel into a fluid inlet interface of a fluid transfer device, the fluid is transferred to an inlet branch of the fluid transfer device fluidically coupled with the fluid inlet interface, which inlet branch splits fluid from the first fluid channel into a plurality of inlet branch channels, the fluid is transferred to a plurality of outlet branches of the fluid transfer device fluidically coupled with the inlet branch channels, where each of the outlet branches splits fluid from a respective one of the inlet branch channels in each case into a plurality of outlet branch channels, and the fluid is transferred to a fluid outlet interface of the fluid transfer device coupled fluidically with the outlet branch channels, at which the fluid is transferred out of the fluid transfer device into the second fluid channel, where the branches and the branch channels are arranged in such a way that the fluid exits from the fluid outlet interface distributed in a two-dimensional manner across the second cross-sectional area.

According to an exemplary embodiment, a fluid transfer device is created as a fluid component which can be interposed between a first channel of smaller diameter and a second channel of larger diameter fluidically connectable thereto. At the inlet interface of this fluid transfer device, the fluid to be transported is fed to an inlet branch, at which the fluid is split up for the first time into various inlet branch channels. Each of the inlet branch channels is then followed, directly or indirectly, by at least one outlet branch, where the split-up fluid is further split up into sub-flows. These individuals sub-flows then flow in each case in well-defined quantities and directions and along defined fluid paths through outlet branch channels, at the ends whereof (for example, lying in a common plane) a portion of the split-up fluid of the fluid outlet interface is made available in each case. The individual defined sub-flows can exit distributed across the entire larger cross-sectional area for further processing. As a result of this defined, hierarchically structured multiplication of the fluid flows broken down into a plurality of branch levels, with the simultaneous reduction of the sub-flows through the individual branch channels, it is possible to achieve a laminar flow with a local flow rate distributed largely uniformly over an area. Problems with jet streams, turbulence or dead volumes can be suppressed or completely eliminated, since the multi-stage branching logic is impressed on the fluid over the whole splitting-up process in each case in a well-defined manner, as a result of which the fluid fanning-out can be controlled in a targeted manner.

Especially in a flow cell of a sample separation path, where a fluid sample already split into a plurality of fractions in a separation device disposed upstream is conventionally subjected to an abrupt transition between a capillary with a small cross-sectional area and a flow cell container with a much larger, likely geometrically different cross-section, it is possible by introducing the fluid transfer device to ensure artifact-free and low-dead-volume decoupling of the fluid into the flow cell. This increases the separation capacity of the respective sample separation device.

Embodiments of the fluid transfer device, the flow cell, the sample separation device and the method are described below.

According to an embodiment, the fluid transfer device can comprise a planar structure (can be formed, for example, as platelets or suchlike), in which the branches and the branch channels are integrated. Such a planar structure can be a platelet-like structure, the thickness whereof is smaller than its other lateral dimensions. The multi-stage, cascade-like splitting-up of the fluid is enabled by such a planar fluid coupling structure along its thickness extension, wherein a transfer to very large cross-sectional areas is also possible as a result of the large main surfaces of the planar structure. Moreover, such a planar structure is very robust and withstands without any problem the high pressures which occur for example with liquid chromatography applications (which can amount at a flow cell to up to 100 bar).

However, according to other embodiments of the invention, it is possible, as an alternative to a planar structure, to constitute the fluid transfer device by an arrangement of branched capillaries or suchlike.

According to an embodiment, the planar structure can comprise a plurality of bonded layers (for example glued or otherwise affixed to one another), which are structured by the formation of openings (for example vias or grooves, through-holes or blind holes) in such a way that the branches or branch channels in fluid communication with one another are formed by the openings of respectively adjacent layers fluid-coupled with one another. Such a laminate arrangement of layers affixed to one another, for example by means of gluing, said layers each comprising a cavity- or hole-structure, can be coupled by bonding to form an integrated network of fluid channels and branches which, according to the embodiment, enable the hierarchical splitting-up of the fluid into ever more individual channels. This is possible with a low outlay and a high degree of design freedom. Moreover, as a result of this planar structure, splitting-up of the flow limited to a narrow lumen at the inlet side into a flow markedly widened two-dimensionally at an outlet side can be brought about conveniently and reliably.

According to an embodiment, the fluid transfer device can comprise the first fluid channel, which can be attached or connected to the fluid inlet interface directly (i.e., without further components disposed in between). According to this embodiment, therefore, the first fluid channel (i.e. a single channel on the inlet side) can be connected free from dead volumes to the inlet interface, as a result of which a turbulent flow is suppressed at the inlet side.

According to an embodiment, the first fluid channel can be a capillary (i.e., a hollow-cylindrical fluid line), in particular, with a circular first cross-sectional area. Such a capillary may be connected to a fluid outlet of a sample separation column, so that the split-up fluid sample can be conveyed through the capillary and introduced into the fluid transfer device.

According to an embodiment, the fluid transfer device may comprise the second fluid channel, which may be attached to the fluid outlet interface directly (i.e., without further components disposed in between). The second fluid channel may be the lumen of a flow cell container, in which a detection of the individual fractions of the fluid sample based on the interaction between the fluid sample and electromagnetic radiation may take place.

According to an embodiment, the second fluid channel may thus be a flow cell container, in particular, with a rectangular (although any other shapes may be incorporated) second cross-sectional area. Since flow cell containers often have a rectangular internal cross-section, the fluid transfer device according to the invention is particularly well suited for such an application, since, according to the invention, not only is a dead-volume-free and at least low-turbulence transition between a small cross-sectional area of inflowing fluid and a larger cross-sectional area of outflowing fluid made possible, but also a geometrical transition between a, for example, circular inlet cross-sectional area and a, for example, rectangular outlet cross-sectional area. An adaptation to any arbitrary geometry of the second fluid channel can be made through a suitable design of the arrangement of the outlet branch channels.

According to an embodiment, the fluid transfer device can comprise a plurality of the intermediate branches coupled fluidically with the inlet branch channels, wherein each of the intermediate branches splits up fluid from a respective one of the inlet branch channels respectively into a plurality of intermediate branch channels, wherein the intermediate branch channels are disposed so as to be coupled fluidically with the plurality of outlet branches, so that each of the outlet branches splits up fluid from a respective one of the intermediate branch channels respectively into a plurality of outlet branch channels, and wherein the intermediate branches and the intermediate branch channels are disposed downstream (in the flow direction of the fluid) of the inlet branch and the inlet branch channels and upstream (in the flow direction of the fluid) of the outlet branches and the outlet branch channels. According to the described embodiment, one or more fluid intermediate planes may be interposed between the plane of the inlet branches and inlet branch channels on the one hand and the plane of the outlet branches and outlet branch channels on the other hand. An additional splitting-up of the flow fractions of the fluid into a further plurality of channels clearly takes place at each of these intermediate planes. Arbitrary scaling of the inlet flow to very large target cross-sectional areas is therefore also possible by selecting a given number of fluid branch planes.

According to an embodiment, the fluid transfer device may thus comprise at least one further arrangement comprising a plurality of further intermediate branches and a plurality of further intermediate branch channels, where the further intermediate branches and the further intermediate branch channels are disposed downstream of the intermediate branches and the intermediate branch channels and upstream of the outlet branches and the outlet branch channels. According to this embodiment, the number of fluid distribution stages may also be greater than 3, e.g., at least 4, or in particular 4, 5, 6, 7, 8, 9 or 10, for example.

According to an embodiment, the branches and the branch channels may be disposed in such a way that the fluid exits from the fluid outlet interface uniformly distributed over the second cross-sectional area (i.e., in particular, at the outlet area of a planar structure). The uniform distribution of the fluid over the entire cross-sectional area may be achieved by the fact that the density of the channels and their cross-sectional areas are accordingly distributed over the entire second cross-sectional area. The density of the outlet branch channels and the cross-sectional area of the outlet branch channels at the fluid outlet interface are preferably identical over the entire second cross-sectional area.

According to an embodiment, the outlet branch channels may be disposed such that the fluid exits from the outlet branch channels with flow directions parallel to one another (which may also be parallel to a flow direction of the fluid at the inlet interface). If the fluid outlet directions, along which the fluid fractions leave the outlet branch channels, are parallel to one another, this enables considerable suppression of undesired turbulence of the fluid at the outlet side. Instead, the fluid will slowly become mixed at the outlet side in an essentially laminar manner and without the formation of turbulence or vortices and will flow onward in the desired direction.

According to an embodiment, the outlet branch channels may be disposed such that the fluid exits from the outlet branch channels at identical flow rates (i.e., exiting fluid volume per time interval). Due to the fact that the flow rates for the individual outlet branch channels are the same, the flow speed of these fluid fractions is equal, which leads to turbulence-free mixing of the individual fluid fractions in the second fluid channel. This is advantageous with regard to the formation of fluid artifacts.

According to an embodiment, at the inlet branch and at each of the outlet branches, in particular, also at each of optional intermediate branches, the fraction of the fluid present in each case may be split up in each case into precisely two branch channels connected downstream. According to this embodiment, a binary branching logic is created, where the fluid is split into two components (e.g., identical magnitude) at each branch. With a number n of branch planes or branch stages, which follow one another in the flow direction of the fluid between the first fluid channel and the second fluid channel, a single inlet flow is split up into $2^n$ outlet sub-flows. A homogeneous, well defined fluid splitting leading to artifact-free further processing of the fluid is thus enabled.

Alternatively, splitting into three or more sub-flows may also be implemented at one or more branches.

According to an embodiment, at the inlet branch and at each of the outlet branches, in particular, also at each of optional intermediate branches, the fraction of the fluid to be split up in each case into equal parts (in particular, into equal volume parts or mass parts) may be split into the branch channels respectively connected downstream. According to this embodiment, the splitting-up of a fluid fraction at a hierarchical stage of connected branch channels that is disposed in each case downstream takes place such that the fluid quantity is split into equal sub-volumes or flow rates. This also suppresses the formation of artifacts in branch channels or at the outlet interface.

The described embodiment may be combined particularly advantageously with another development, where the total length of the individual flow paths, which each of the fluid fractions covers between the inlet interface and a respective one of the outlet interface-side ends of the outlet branch channels, is equal. Especially when all these channels are constituted with the same cross-sectional area, this leads to identical flow times of all the fractions of the fluid through the fluid transfer device, so that an undesired time-related splitting-up or time-related shift of different fluid fractions is avoided.

It should be emphasized that the fluid flow direction of the fluid to be transferred from the first fluid channel into the second fluid channel is described here in a way that relates to the widening of the fluid from the first cross-sectional area to the second cross-sectional area. A person of ordinary skill in the art will, however, understand that the fluid transfer device of various embodiments may also be operated in the inverse flow direction of the fluid, i.e., that a fluid is made available via the second cross-sectional area at the outlet interface. As a result of the flow of the fluid from the outlet interface to the inlet interface, branching does not then arise, but instead a successive unification of individual fluid flows. According to an example of embodiment of the invention, the fluid transfer device may thus be employed or used in such a way that the fluid is concentrated or focused from the large second cross-sectional area to the small first cross-sectional area. The fluid flow direction merely has to be inverted for this purpose.

According to an embodiment, the detection device of the flow cell may be set up for detecting separated fractions of the fluid. The fluid may thus be fed in an already separated form to the detection device. This actual separation may be accomplished upstream of the flow cell by a separation element, such as for example a chromatographic separation column. If the individual fractions of the fluid or the fluid sample, for example, a biological or chemical sample, are fed to the detection device, the latter may carry out the detection during the flow of the fluid through the second fluid channel.

According to an embodiment, the detection device may be an optical detection device, a fluorescence detection device, an absorption detection device, a refractive index detector or a resistance detection device. The detection preferably takes place by the fact that electromagnetic primary radiation (for example in the UV region or in the visible region) is radiated onto the already separated fluid sample, and that electromagnetic secondary radiation, which is generated by the interaction of the electromagnetic primary radiation with the fluid sample, is detected by a radiation detection device of the detection device and is subsequently evaluated. Since the interaction characteristic (in particular, the fluorescence properties) of different fractions of the fluid sample with electromagnetic radiation is different, each individual fraction of the fluid sample may thus be ascertained qualitatively and quantitatively. Other detection methods are of course also possible. When electromagnetic radiation is used, it is particularly preferable that the flow cell container is produced from a transparent material (such as for example quartz glass), when the fluid sample flows in the second fluid channel in the interior of the flow cell container. The flow cell should therefore consist of a transparent material. Quartz glass may be used advantageously because it is still transparent in the UV region.

According to an embodiment, the sample separation device may comprise a heat exchanger, which comprises a thermally conductive heat exchange body comprising the first fluid channel for the passage of the fluid and a third fluid channel for the passage of the fluid after it exits from the flow cell, where the first fluid channel and the third fluid channel are arranged in the heat exchange body such that, during the passage of a first fraction of the fluid through the first fluid channel and during the passage of a second fraction of the fluid through the second fluid channel, the first fraction and the second fraction may be brought together in a thermal exchange. The heat exchanger may advantageously comprise a plurality of cooling elements (for example cooling fins, cooling ribs or Peltier cooling elements) and/or heating elements (for example Peltier heating elements), which are disposed separately and thermally spaced apart from one another in a flow direction of at least one of the first and the second fraction of the fluid and are coupled thermally with the heat exchange body in such a way that heat given off by the first fraction and/or the second fraction may be carried away by the cooling elements or heat given off to the first fraction and/or the second fraction may be supplied by the heating elements. The first fluid channel conveys the fluid fed to the flow cell, the second fluid channel conveys the fluid inside the flow cell, and the third fluid channel conveys the fluid carried away from the flow cell. The provision of such a counter-flow heat exchanger, which brings hot fluid upstream of the flow cell into a thermal interaction with cold fluid downstream of the flow cell, may suppress excessively large temperature differences along the fluid path. The latter are a cause of deterioration in the separation performance.

According to an embodiment, the heat exchange body may be constituted in one piece or integrally with a planar structure, for example, the planar structure described above, of the fluid transfer device. The branches and the branch channels may be integrated in the planar structure. According to this embodiment, the planar structure in which the various branches and branch channels are introduced and the heat exchanger may advantageously be constituted in a single common structure, i.e., in one piece in a common body. This leads to a miniaturized arrangement of a liquid chromatography device with an integrated fluid-widening and heat exchange capability. The sample separation device may thus be constituted in a compact manner.

The sample separation device may be a micro-fluid measuring device, a life-science device, a liquid chromatography device, a High Performance Liquid Chromatography (HPLC) device, a gas chromatography device, an electrophoresis device and/or a gel electrophoresis device. Many other applications are however possible.

The sample separation device may comprise a pump for moving a mobile phase. Such a pump may for example be equipped to pump the mobile phase through the system at a high pressure, for example, several 100 bar up to 1000 bar and more. Alternatively, or in addition, the sample separation device may comprise a sample injector for injecting the fluid sample into a mobile phase. Such a sample injector may comprise a needle in a seat of a corresponding liquid path, which needle may travel out of this seat in order to pick up a fluid sample and which injects the fluid sample into the system after reintroduction into the seat. Alternatively, or in addition, the sample separation device may comprise a sample fractioner for fractioning the separated components. Such a fractioner may for example convey the different components into different liquid containers. The analyzed sample may however also be fed to a waste container.

BRIEF DESCRIPTION OF THE DRAWINGS

The illustrative embodiments are understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIG. 7 is a top plan view of individual layers of a multi-layer planar structure of a fluid transfer device, according to a representative embodiment.

FIG. 8 is a top plan view of individual layers of a multi-layer planar structure of a fluid transfer device, according to a representative embodiment.

FIG. 9 is a top plan view of individual layers of a multi-layer planar structure of a fluid transfer device, according to a representative embodiment.

FIG. 10 is a top plan view of individual layers of a multi-layer planar structure of a fluid transfer device, according to a representative embodiment.

FIG. 11 is a top plan view of individual layers of a multi-layer planar structure of a fluid transfer device, according to a representative embodiment.

FIG. 12 is a block diagram showing part of an HPLC system, in which a heat exchanger and a planar fluid transfer device are provided in integrated form, according to a representative embodiment.

DETAILED DESCRIPTION

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings. Generally, it is understood that the drawings and the various elements depicted therein are not drawn to scale.

Figure 1:
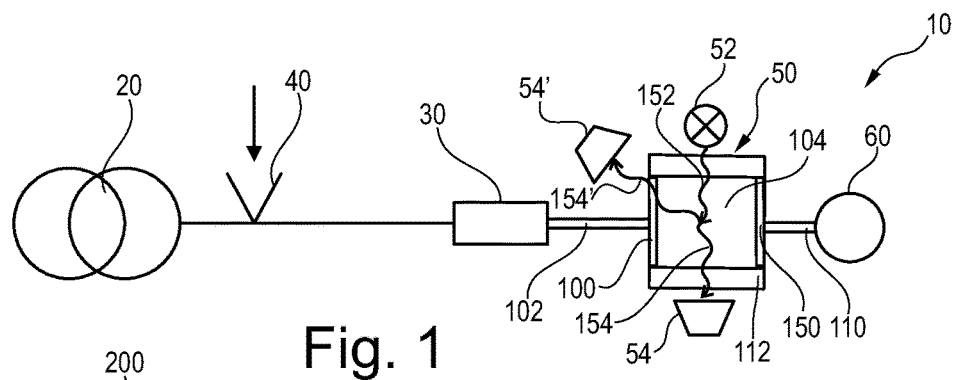
FIG. 1 is a block diagram showing an HPLC system, according to a representative embodiment.

FIG. 1 is a block diagram showing the basic structure of an HPLC system 10, according to a representative embodiment, such as may be used for example for liquid chromatography, for example. A pump 20 drives a mobile phase through a separation device 30 (for example, a chromatographic column), which contains a stationary phase. A sample delivery unit 40 is disposed between the pump 20 and the separation device 30 in order to introduce a sample fluid into the mobile phase. The stationary phase of separation device 30 is configured to separate components of the sample fluid. A detector 50, which may be a flow cell or other detection cell, for example, detects separate components of the sample fluid, and a fractioning device 60 may be provided to deliver separated components of the sample fluid, for example into containers provided for the purpose or to a drain.

Whereas a fluid path between pump 20 and separation device 30 is typically under high pressure, the sample fluid, under normal pressure, is first fed into a region of sample delivery unit 40 that is separated from the fluid path, a so-called sample loop, which then in turn introduces the sample fluid into the fluid path being under high pressure. When the sample fluid initially under normal pressure in the sample loop is switched into the fluid path being under high pressure, the content of the sample loop is abruptly (typically in the region of milliseconds) brought to the system pressure of HPLC system 10.

Disposed downstream of separation device 30 and upstream of fractioning device 60 is the detector 50, at which the fractions of the fluid sample separated by separation device 30 are detected. For this purpose, the already separated fluid is introduced via a capillary, first fluid channel 102, which leads from separation device 30 to detector 50, into a fluid transfer device 100 according to a representative embodiment. Fluid transfer device 100 transfers the fluid from the first fluid channel 102 into the interior of a flow cell container 112, in which the fluid sample flows along a second fluid channel 104. Provided at the end of second fluid channel 104 is a fluid outlet opening 150 in flow cell container 112, at which the fluid flows into another capillary, third fluid channel 110. The fractioning device 60 is then disposed downstream of the third fluid channel 110. In the interior of flow cell container 112, the fluid already separated into the individual fractions interacts with UV light 152, which is generated by an ultraviolet light source 52. The UV-light interacts in flow cell container 112 with the individual fractions of the split-up fluid, so that secondary light 154 is detected at a UV absorption detector 54. The output of UV absorption detector 54 is indicative of the nature and concentration of the individual fractions.

A fluorescence measurement is also possible as an alternative to the described absorption measurement using UV absorption detector 54. In this case, secondary light 154' is measured as that which is generated by fluorescence of the sample when primary light 152 is radiated. As shown, a corresponding fluorescence detector 54' may be disposed at a suitable angle, e.g., in the reverse direction in the depicted example, in order to detect fluorescence radiation in the form of secondary light 154'. With such a fluorescence measurement, it is optionally possible to use a reference detector, for example at the position of UV absorption detector 54, in order to evaluate its signal together with the fluorescence signal (for example, in order to compensate for fluctuations in the emission intensity of light source 52).

According to the depicted representative embodiment, fluid transfer device 100 is constituted such that fluid is transferred from relatively narrow first fluid channel 102, which may have a circular (or substantially circular) small internal cross-section, into relative wide second fluid channel 104, which may have a rectangular (or substantially rectangular) and much larger internal cross-section. Of course, other cross-sectional shapes may be implemented without departing from the scope of the present teachings.

Before representative embodiments of fluid transfer device 100 are described in greater detail, several basic considerations are presented, based on the representative embodiment.

In detector 50 of HPLC system 10, the fluid flows are to be transferred from first fluid channel 102 having a smaller cross-sectional area into second fluid channel 104 of the flow cell with a large internal diameter. The challenge associated therewith is particularly great for fluorescence detection, since particularly large flows cell volumes are involved.

According to a conventional solution concept of such a fluid interface, a transition piece with a conically widening lumen is interposed between capillary and flow cell lumen. In such a conical intermediate section, a transfer between the capillary with a small internal diameter (for example 12 μm to 18 μm) and the larger cross-sectional area of the flow cell body, which may have a rectangular shape, is carried out. A high dead volume may however be formed in such a conical transition section, which undesirably remains free from any fluid flow. The fluid is then injected into the flow cell body, wherein the internal volume is used only partially for the transport of the fluid and partially remains free from the fluid. This often leads to poor detection of the individual fractions of the fluid sample in the flow cell.

Another conventional approach consists in introducing a perforated plate into the conical transition section between capillary and flow cell body, with which jet streams may however only be slightly suppressed. Moreover, this measure leads to turbulence, which may also lead to poor detection of the individual fractions of the fluid sample in the flow cell.

Compared with such conventional approaches, various embodiments herein are based on the fact that the fluid is transferred from first fluid channel 102 with a small cross-sectional area by a gradually branching fluid network into flow cell body 112 with a larger cross-section, by which a very small dead volume and only very small peak broadening may be achieved. The chromatographic separation capacity may be increased on account of the small dead volume. The suppression of jet streams makes it possible to utilize essentially the whole cell volume for detection. Moreover, such a solution may be advantageously combined with a heat exchanger on the same planar structure, on which fluid transfer device 100 is also formed. This leads to a particularly compact arrangement.

Figure 2:
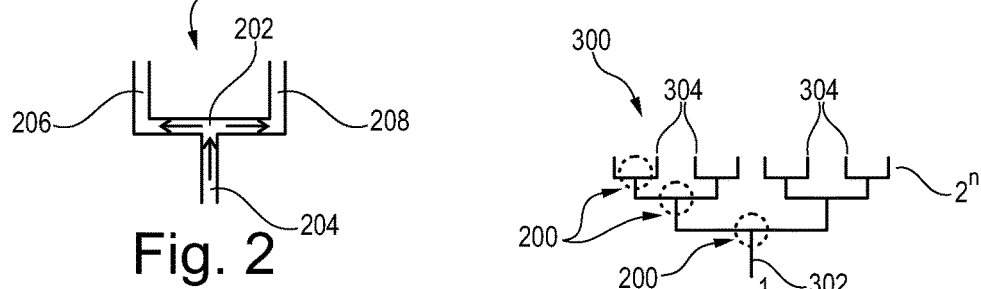
FIG. 2 is a block diagram showing the splitting-up of a fluid fraction into two fluid sub-fractions at a branch of a fluid transfer device, according to a representative embodiment.

FIG. 2 shows a flow branch 200, which may be implemented as a basic component in a fluid transfer device 100 according to a representative embodiment. Flow branch 200 splits an inlet flow of a fluid (a liquid and/or a gas, in which solid components also may be contained) at a T-piece 202 from a feed lumen 204 in equal parts into two discharge lumens 206, 208. In other words, the inlet flow is split up by flow branch 200 into two equal outlet flows.

Figure 3:
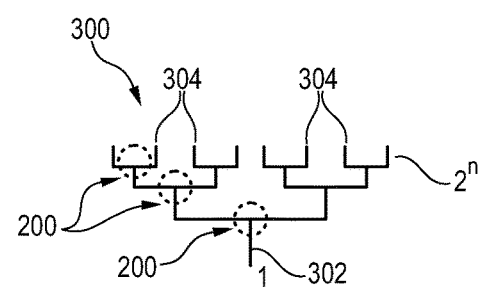
FIG. 3 is a block diagram showing a hierarchical multi-stage branching of fluid fractions in a fluid transfer device, according to a representative embodiment.

FIG. 3 shows a branch network 300, which is constituted by a plurality of flow branches 200. Branch network 300 with n hierarchically disposed branch planes, where n is a positive integer (n=3 in the present example), makes it possible for a fluid made available at a single fluid inlet 302 to be made available split up into uniform portions at $2^n$ fluid outlets 304. In other words, by repeating the fluid branch diagram according to FIG. 2, $2^n$ identical fluid flows are generated at outlet side from a single inlet-side fluid flow and may then flow into a flow cell volume.

Figure 4:
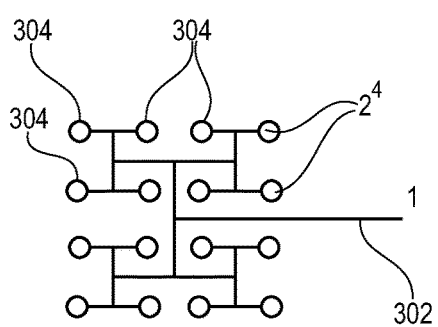
FIG. 4 is a block diagram showing how, with a hierarchical multi-stage branching of a fluid into sub-flows, a uniform distribution of the fluid over an essentially two-dimensional area is enabled, according to a representative embodiment.

FIG. 4 is an example of n=4 branch planes or branch stages, and shows how sub-flows may be generated at $2^4$ fluid outlets 304 from a single fluid flow at fluid inlet 302, where fluid outlets 304 are disposed in such a way that the sub-flows are distributed equally over the entire two-dimensional area of a fluid outlet interface of the flow cell body.

Figure 5:
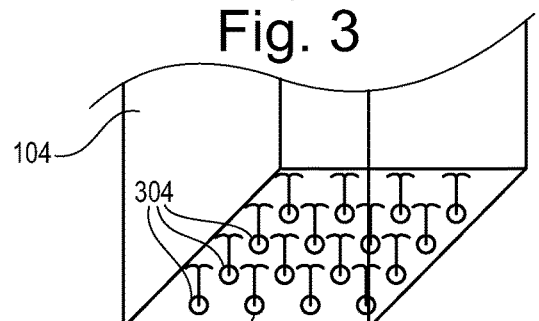
FIG. 5 is a plan view showing how a plurality of fluid sub-flows exit parallel to one another from a fluid outlet interface of a fluid transfer device, according to a representative embodiment.

FIG. 5 shows $2^4$ fluid outlets 304 with parallel-flowing 16 sub-flows according to FIG. 4 at an inlet to second fluid channel 104. By a fluid transfer device according to the embodiments, which may be constituted based on the basic principle of FIG. 2 to FIG. 5, a fluid flow may thus be transferred without formation of a dead volume from narrow first fluid channel 102 into a flow cell having a larger cross-section.

A plate-shaped fluid transfer device 100 according to a representative embodiment is described below making reference to FIG. 6. Fluid transfer device 100 is represented in a cross-sectional view in FIG. 6. Because many flow branches are formed in a complex branched arrangement of capillaries, the arrangement of the flow branches is depicted in a planar structure in this embodiment. Compared with an arrangement comprising capillaries, this further enables a miniaturization, since micro-structuring techniques may be used to produce fluid channels in layers of the planar structure.

Figure 6:
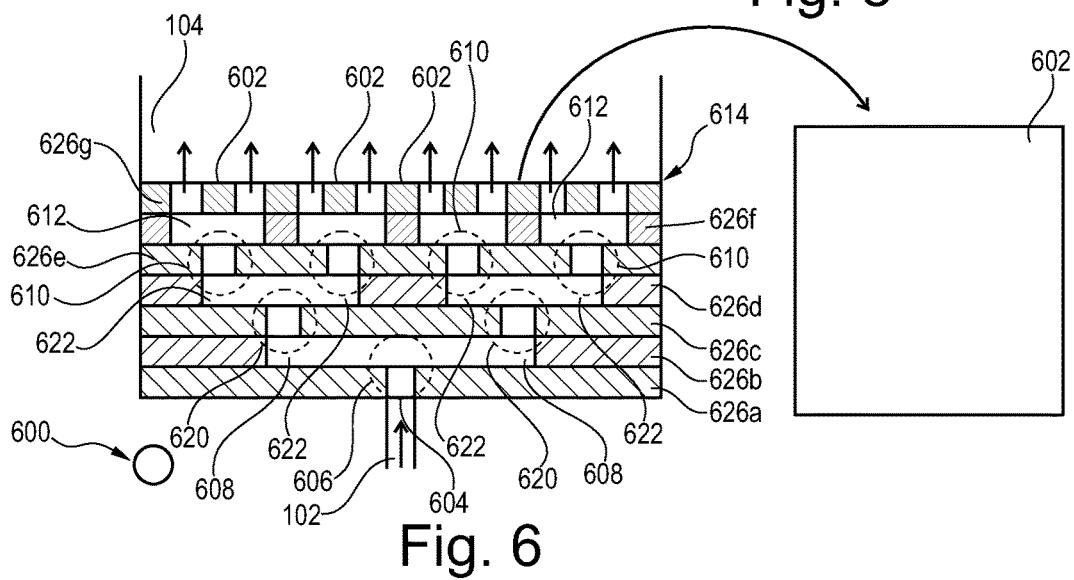
FIG. 6 is a block diagram showing a cross-sectional view of a planar structure comprising bonded layers, in which openings coupled with one another fluidically form a hierarchically multi-stage arrangement of branches and branch channels, according to a representative embodiment.

FIG. 6 thus shows a fluid transfer device 100 according to a representative embodiment for transferring a fluid from a first fluid channel 102 with a first circular cross-sectional area 600 at the outlet side into a second fluid channel 104 with a second rectangular cross-sectional area 602 at the inlet side. As is shown in two top views of cross-sectional areas 600, 602, first cross-sectional area 600 differs from second cross-sectional area 602, not only with regard to its size, but also with regard to its geometry. As is described below, fluid transfer device 100 is capable of accomplishing not only a transfer between cross-sectional areas of differing size, but also between different cross-sectional shapes.

With reference to FIG. 1, for example, first fluid channel 102 is a capillary, in which the fluid is conveyed from a separation device 30 to fluid transfer device 100. Second fluid channel 104 with a rectangular cross-sectional area is the lumen in a flow cell container 112.

Fluid transfer device 100 has a fluid inlet interface 604, at which the fluid is transferred from first fluid channel 102 into fluid transfer device 100. Fluid transfer device 100 further has an inlet branch 606, which is coupled fluidically with fluid inlet interface 604 and which splits the fluid from first fluid channel 102 uniformly into connected inlet branch channels 608. As can also be seen from FIG. 6, each of inlet branch channels 608 is coupled fluidically with an associated intermediate branch 620. At each of intermediate branches 620, the fluid already previously split is again split uniformly into connected intermediate branch channels 622, each one of which leads to an associated outlet branch 610. At each outlet branch 610, the fluid quantity made available is again split into identical parts into connected outlet branch channels 612. In the described manner, the fluid is successively split up repeatedly into sub-flows in multiple stages, where the splitting into sub-flows is accompanied at the same time by the splitting of the fluid flow over a gradually increasing cross-sectional area. Finally, the fluid is made available split over the entire cross-sectional area of second fluid channel 104, as a result of which the transfer between first fluid channel 102 and second fluid channel 104 takes place without dead volumes and without undesired turbulent flow effects.

As emerges from FIG. 6, fluid transfer device 100 may be constituted as a compact planar structure. By openings in layers 626a to 626g bonded to one another, a plate-shaped arrangement with integrated flow paths is provided, which also withstands the high pressures of 2000 bar and more, to which flow transfer device 100 may be subjected in a liquid chromatography device. By the fact that first fluid channel 102 is connected at the inlet side directly to fluid inlet interface 604, and second fluid channel 104 is directly connected at the outlet side to fluid outlet interface 614, dead volumes at these two transitions are avoided. Although only a single intermediate stage is provided in FIG. 6, and therefore a total of three branch stages (inlet, intermediate and outlet stage), a person of ordinary skill in the art will understand that more or fewer branch stages (and thus corresponding planes) may be incorporated without departing from the scope of the present teachings. In fluid transfer device 100 according to FIG. 6, the fluid cross-sectional areas and the lengths of the flow paths, through which the individual fluid fractions flow between fluid inlet interface 604 and fluid outlet interface 614, are identical. This leads to substantially uniform splitting of the fluid into each individual one of these paths, where the individual fluid fractions exit at fluid outlet interface 614 at the same speed and in the same flow directions. Undesired turbulence is thus avoided and a laminar and artifact-free mixing of the individual fluid flows at the outlet side is thus promoted. Alternatively, it is of course possible to provide flow paths of differing lengths, different fluid cross-sections and/or more or fewer branch channels at a given branching, which may lead to substantially non-uniform splitting, without departing from the scope of the present teachings.

FIG. 7 to FIG. 11 show top views of individual planar layers 626a to 626e, such as can be used with a five-layer planar structure (such as the bottom five planes according to FIG. 6).

At an inlet layer 626a shown in FIG. 7, a single central opening 702 is provided, which is connected to first fluid channel 102.

In a first intermediate layer 626b shown in FIG. 8, a larger central opening 802 is provided, which is brought into fluid communication with opening 702 when first intermediate layer 626b is bonded to inlet layer 626a.

A second intermediate layer 626c with four symmetrically disposed rectangular openings 902 is shown in FIG. 9. Openings 902 are brought into fluid communication with opening 802, so that layers 626a, 626b and 626c provide together a branching of an inlet channel into four intermediate channels.

FIG. 10 shows a third intermediate layer 626d with four symmetrically disposed rectangular openings 1002, which are larger than those according to FIG. 9. Openings 1002 are brought into fluid communication with openings 902 after appropriate bonding of intermediate layers 626c and 626d.

FIG. 11 shows an outlet layer 626e with 16 rectangular openings 1102 disposed in matrix form, which are brought into fluid communication with openings 1002, thus splitting a given respective fluid flow into four channels corresponding to respective four associated openings 1102.

By the superposition and bonding of layers 626a to 626e from FIG. 7 to FIG. 11, a five-layer planar arrangement may be obtained, which may be used as a fluid transfer device according to a representative embodiment.

FIG. 12 shows, in magnified form, a part of HPLC system 10 from FIG. 1, in which a counter-flow heat exchange device with forced air cooling is also described.

In the configuration according to FIG. 12, a heat exchanger is provided between an outlet of separation device 30 and an inlet of fractioning device 60, as will be described in greater detail below. The heat exchanger produces a temperature equalization between hot sample at the outlet of separation device 30 and colder sample at an outlet of detector 50.

The heat exchanger contains a heat exchange body 80 made of a good thermally conductive material, which comprises a first lumen 82 (or first fluid channel 102) for the passage of a first fluid coming out of separation device 30 and a second lumen 84 (or third fluid channel 110) for the passage of a second fluid coming out of detector 50. First lumen 82 and second lumen 84 are brought into a counter-flow heat exchange by thermally conductive heat exchange body 80, in such a way that, when the first fluid passes through first lumen 82 and the second fluid passes through second lumen 84, the first fluid and the second fluid may exchange thermal energy with one another. Affixed externally to thermally conductive heat exchange body 80 is a plurality of parallel cooling fins 86, which are disposed separately and thermally spaced apart from one another along a flow direction (see arrow) of the first and the second fluid, and are thermally coupled with heat exchange body 80 in such a way that heat given off by the first fluid and by the second fluid may be carried away to the exterior by cooling elements 86. As can be seen from the opposite directions of the two arrows in FIG. 12, heat exchange body 80 is constituted as a counter-flow heat exchange body, i.e., the flow directions of the first and second fluids through the first and second lumens 82 and 84 are opposed.

According to embodiments, therefore, a low-cost, small-volume cooling mechanism can thus be provided, which cools fluid directly before detector 50, so that a flow path is kept short overall. Passive cooling is thus created through heat exchanger 80, first lumen 82, second lumen 84 and cooling fins 86, which enables temperature equalization between the hot liquid from separation device 30 and the colder liquid following detector 50. In addition, there is provided in the form of cooling fins 86 a measure for efficiently carrying away the thermal energy imparted to cooling fins 86, as a result of which a selective increase in the heat losses is enabled. On account of the restricted space in which the heat exchange device is provided, the cooling fins 86 may be provided finger-shaped, for example. Cooling fins 86 are disposed over the entire length of heat exchange body 80, said length being vertical in the orientation depicted in FIG. 1. A large quantity of heat is carried away by a cooling fin 86 in the thermal exchange with a hot fluid. A cooling fin 86 at a cold outlet, on the other hand, has the object of ensuring an overall low temperature of the fluid, and the heat exchanger principle may thereby be used to advantage.

FIG. 12 shows that, as is described in greater detail below, the hot liquid with a temperature of 95° C., for example, coming from separation device 30 is cooled down overall to 70° C., for example, by a counter-flow heat exchanger principle, before it is conveyed in the direction of waste 60. The temperature is 30° C., for example, in a region of detector 50. The cooling takes place overall, for example, from 95° C. to 70° C. through the passive cooling via cooling ribs or cooling fins 86. The temperature in the region of detector 50 is lower (for example at 30° C.) due to the counter-flow heat exchanger principle.

As is further shown in FIG. 12, the detector 50 in the described embodiment is formed by a light source 52 and a light detector 54, which detects light that originates from light source 52 and has not been absorbed or fluoresced by the fluid. Thermal malfunctions of detector 50 are avoided on account of the heat flow architecture according to FIG. 12. The thermal decoupling of individual cooling fins 86 ensures that the different heat dissipation characteristics of the different cooling fins 86 are different (see the arrow in FIG. 12). A distinction needs to be made here between heat transfer between the hot liquid in the first lumen 82 and the cooler liquid in the lumen 84 on the one hand, and dissipation of heat to the surroundings on the other hand. The former is accomplished by the heat exchange via heat exchange body 80 of the liquids present in the counter-flow exchange in the first and second lumens 82 and 84, whilst the latter is produced by cooling fins 86 and their thermal decoupling or weak thermal coupling with one another.

FIG. 12 also shows a further advantageous measure, i.e., an air flow generation unit 92, which generates air flow 94 which carries away the thermal energy from cooling fins 86 and dissipates it to the exterior. Air flow 94 is therefore advantageously conveyed along cooling fins 86. Electronics (not shown in the figures) in HPLC system 10 or light source 52 of detector 50 may advantageously be cooled by the same air flow 94, by which cooling fins 86 are also cooled. This permits a small and energy-saving arrangement.

FIG. 12 clearly shows that both the heat exchanger and fluid transfer device 100 are integrated in a common planar structure. This leads to a compact design and cost-effective production of the arrangement according to FIG. 12.

A measurement setup is shown in FIG. 12, where detector 50 measures the absorption of light through the sample in transmission. Alternatively, a fluorescence measurement is also possible here, as described by reference to FIG. 1.

It should be noted that the terms "comprise" and "comprising' do not exclude other elements and that the term "a/an" does not exclude a plurality. Elements which are described in connection with different embodiments may also be combined. It should also be noted that reference numbers in the claims should not be interpreted as limiting the scope of protection of the claims.

While the disclosure references illustrative embodiments, it will be apparent to those skilled in the art that various changes and modifications may be made without departing from the spirit and scope of the present teachings. Therefore, it should be understood that the above embodiments are not limiting, but illustrative.

What is claimed is:

1. A fluid transfer device for transferring a fluid from a first fluid channel with a first cross-sectional area at an outlet side into a common second fluid channel with a second cross-sectional area at an inlet side, the second cross-sectional area being larger than the first cross-sectional area, the fluid transfer device comprising:
    a fluid inlet interface at which the fluid is transferable out of the first fluid channel into the fluid transfer device;
    an inlet branch fluidically coupled with the fluid inlet interface, and configured to split the fluid from the first fluid channel into a plurality of inlet branch channels;
    a plurality of outlet branches fluidically coupled with the inlet branch channels, wherein each of the outlet branches is configured to split the fluid from the inlet branch channels into a respective plurality of outlet branch channels; and
    a fluid outlet interface comprising a plurality of outlet openings a) fluidically coupled with the outlet branch channels and b) forming a two-dimensional array of the outlet openings by which the fluid outlet interface is fluidically coupled with the common second fluid channel in a two-dimensional manner across the second cross-sectional area, the fluid outlet interface configured to transfer the fluid in the outlet branch channels into the common second fluid channel via the outlet openings,
    wherein the inlet branch, the outlet branches, the inlet branch channels and the outlet branch channels are disposed such that the fluid exits from the fluid outlet interface, distributed in a two-dimensional manner across the second cross-sectional area.

2. The fluid transfer device according to claim 1, wherein:
    the inlet branch, the outlet branches, the inlet branch channels and the outlet branch channels are disposed such that the fluid exits, distributed essentially uniformly across the second cross-sectional area, from the fluid outlet interface;
    the outlet branch channels are disposed such that the fluid exits from the outlet branch channels with flow directions parallel to one another;
    the outlet branch channels are disposed such that the fluid exits from the outlet branch channels at identical flow rates;
    at the inlet branch and at each of the outlet branches, a fraction of fluid to be split in each case is split into two branch channels in each case connected downstream; or
    at the inlet branch and at each of the outlet branches, the fraction of fluid to be split up in each case is split in equal parts into the branch channels connected downstream.

3. The fluid transfer device according to claim 1, further comprising:
    a planar structure, in which the inlet and outlet branches and the inlet and outlet branch channels are integrated.

4. The fluid transfer device, according to claim 3, wherein the planar structure comprises a plurality of bonded layers, which, while forming openings, are structured such that the inlet branch, the outlet branches, the inlet branch channels and the outlet branch channels are formed by the openings of respectively adjacent bonded layers of the plurality of bonded layers fluid-coupled with one another.

5. The fluid transfer device according to of claim 1, wherein the first fluid channel is attached directly to the fluid inlet interface.

6. The fluid transfer device according to claim 5, wherein the first fluid channel is a capillary, and the first cross-sectional area is substantially circular.

7. The fluid transfer device according to claim 1, wherein the second fluid channel is attached directly to the fluid outlet interface.

8. The fluid transfer device according to claim 7, wherein the second fluid channel comprises a flow cell container and the second cross-sectional area is substantially rectangular.

9. The fluid transfer device according to claim 1, further comprising:
    a plurality of intermediate branches fluidically coupled to the inlet branch channels, and configured to split fluid from the inlet branch channels into a plurality intermediate branch channels,
    wherein the intermediate branch channels are fluidically coupled to the outlet branches, so that each of the outlet branches is configured to split the fluid from the intermediate branch channels into the outlet branch channels, and
    wherein the intermediate branches and the intermediate branch channels are disposed downstream of the inlet branch and the inlet branch channels and upstream of the outlet branches and the outlet branch channels.

10. The fluid transfer device according to claim 9, further comprising:
    a plurality of further intermediate branches and further intermediate branch channels, wherein the further intermediate branches and the further intermediate branch channels are disposed downstream of the intermediate branches and the intermediate branch channels and upstream of the outlet branches and the outlet branch channels.

11. A flow cell for detecting a fluid feedable from a first fluid channel having a first cross-sectional area at an outlet side, the flow cell comprising:
    a common second fluid channel having a second cross-sectional area at an inlet side, the second cross-sectional area being larger than the first cross-sectional area;
    a fluid transfer device for transferring the fluid from the first fluid channel into the common second fluid channel, said fluid transfer device comprising,
        a fluid inlet interface at which the fluid is transferable out of the first fluid channel into the fluid transfer device,
        an inlet branch fluidically coupled with the fluid inlet interface, and configured to split the fluid from the first fluid channel into a plurality of inlet branch channels,
        a plurality of outlet branches fluidically coupled with the inlet branch channels, wherein each of the outlet branches is configured to split the fluid from the inlet branch channels into a respective plurality of outlet branch channels, and a fluid outlet interface comprising a plurality of outlet openings a) fluidically coupled with the outlet branch channels and b) forming a two-dimensional array of the outlet openings by which the fluid outlet interface is fluidically coupled with the common second fluid channel in a two-dimensional manner across the second cross-sectional area, the fluid outlet interface configured to transfer the fluid in the outlet branch channels into the common second fluid channel via the outlet openings, wherein the inlet branch, the outlet branches, the inlet branch channels and the outlet branch channels are disposed such that the fluid exits from the fluid outlet interface, distributed in a two-dimensional manner across the second cross-sectional area; and a detection device configured to detect information indicative of a property of the fluid by interacting with the fluid flowing along the second fluid channel.

12. The flow cell according to claim 11, wherein the detection device is configured to detect separated fractions of the fluid.

13. The flow cell according to claim 12, wherein the detection device is selected from a group consisting of an optical detection device, a fluorescence detection device, an absorption detection device, a refractive index detector and a resistance detection device.

14. A sample separation device for separating fractions of a fluid, the sample separation device comprising:
a separation device for separating different fractions of the fluid, the separated fractions of the fluid being fed to a first fluid channel having a first cross-sectional area at an outlet side; and
a flow cell according to claim 11 for detecting the fluid which is feedable from the first fluid channel.

15. The sample separation device according to claim 14, wherein:
the sample separation device is selected from a group consisting of a micro-fluid measuring device, a life science device, a liquid chromatography device, an HPLC, a gas chromatography device, an electrophoresis device and a gel electrophoresis device;
the sample separation device comprises a pump for moving a mobile phase, into which the fluid can be injected;
the sample separation device comprises a sample delivery unit for injecting the fluid into a mobile phase;
the separation device comprises a separation column for separating different fractions of the fluid; or
the sample separation device comprises a sample fractioning device for fractioning the separated fractions.

16. The sample separation device according to claim 14, further comprising:
a heat exchanger comprising a thermally conductive heat exchange body, which comprises the first fluid channel for the passage of the fluid and a third fluid channel for passage of the fluid after exiting from the flow cell, wherein the first fluid channel and the third fluid channel are fitted to the heat exchange body in such a way that a respective first fraction of the fluid in the first fluid channel and a respective second fraction of the fluid in the second fluid channel are brought together in a thermal exchange.

17. The sample separation device according to claim 16, wherein the heat exchanger comprises a plurality of cooling elements or heating elements, which are disposed separately and thermally spaced apart from one another in a flow direction of at least one of the first and second fractions of the fluid, and are coupled thermally with the heat exchange body such that heat given off by at least one of the first fraction and the second fraction is carried away by the cooling elements or heat given off to the at least one of the first fraction and the second fraction is supplied by the heating elements.

18. The sample separation device according to claim 16, wherein the heat exchange body is integrally formed with a planar structure of the fluid transfer device, in which the planar structure, the branches and the branch channels are integrated.

19. A method for transferring a fluid from a first fluid channel having a first cross-sectional area at an outlet side into a common second fluid channel having a second cross-sectional area at an inlet side, the second cross-sectional area being larger than the first cross-sectional area, the method comprising:
transferring the fluid out of the first fluid channel into a fluid inlet interface of a fluid transfer device;
transferring the fluid to an inlet branch of the fluid transfer device, which inlet branch is coupled fluidically with the fluid inlet interface and splits fluid from the first fluid channel into a plurality of inlet branch channels; and
transferring the fluid to a plurality of outlet branches of the fluid transfer device, said plurality of outlet branches being coupled fluidically with the inlet branch channels, wherein each of the outlet branches splits fluid from a respective one of the inlet branch channels into a plurality of outlet branch channels; and
transferring the fluid to a fluid outlet interface of the fluid transfer device, the fluid outlet interface comprising a plurality of outlet openings, a) coupled fluidically with the outlet branch channels and b) forming a two-dimensional array of the outlet openings by which the fluid outlet interface is fluidically coupled with the common second fluid channel in a two-dimensional manner across the second cross-sectional area, and configured to transfer the fluid out of the fluid transfer device into the common second fluid channel via the outlet openings,
wherein the inlet and outlet branches and the inlet and outlet branch channels are disposed such that the fluid exits, distributed in a two-dimensional manner across the second cross-sectional area, from the fluid outlet interface.

* * * * *